United States Patent
Walls et al.

(10) Patent No.: US 10,198,852 B2
(45) Date of Patent: Feb. 5, 2019

(54) DIGITAL PORE ALTERATION METHODS AND SYSTEMS

(71) Applicant: HALLIBURTON ENERGY SERVICES, INC., Houston, TX (US)

(72) Inventors: Joel Walls, Houston, TX (US); Abraham Grader, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 14/863,171

(22) Filed: Sep. 23, 2015

(65) Prior Publication Data

US 2016/0093094 A1   Mar. 31, 2016

Related U.S. Application Data

(60) Provisional application No. 62/055,242, filed on Sep. 25, 2014.

(51) Int. Cl.
| | |
|---|---|
| G06T 15/08 | (2011.01) |
| H01J 37/28 | (2006.01) |
| G01N 23/2258 | (2018.01) |
| G01N 15/08 | (2006.01) |
| G01V 99/00 | (2009.01) |

(52) U.S. Cl.
CPC .......... *G06T 15/08* (2013.01); *G01N 15/088* (2013.01); *G01N 23/2258* (2013.01); *H01J 37/28* (2013.01); *G01N 2015/0846* (2013.01); *G01N 2223/305* (2013.01); *G01N 2223/616* (2013.01); *G01V 99/00* (2013.01)

(58) Field of Classification Search
None
See application file for complete search history.

(56) References Cited

U.S. PATENT DOCUMENTS

| | | | |
|---|---|---|---|
| 4,783,751 A | 11/1988 | Ehrlich et al. | |
| 2007/0203677 A1 | 8/2007 | Awwiller | |
| 2009/0259446 A1* | 10/2009 | Zhang | E21B 49/00 703/2 |
| 2011/0056271 A1* | 3/2011 | Larter | G01N 33/2823 73/23.37 |
| 2011/0295580 A1 | 12/2011 | Sisk et al. | |
| 2012/0310614 A1* | 12/2012 | Beattie | E21B 43/16 703/10 |
| 2013/0259190 A1 | 10/2013 | Walls et al. | |

(Continued)

OTHER PUBLICATIONS

Andrä, Heiko, et al. "Digital rock physics benchmarks—Part I: Imaging and segmentation." Computers & Geosciences 50 (Sep. 2012): 25-32.*

(Continued)

*Primary Examiner* — Vu Le
*Assistant Examiner* — Tracy Mangialaschi
(74) *Attorney, Agent, or Firm* — Chamberlain Hrdlicka

(57) ABSTRACT

A method includes receiving images of a rock sample. The method also includes modifying a set of voxels related to one or more of the received images by applying a digital pore growing operation that changes non-pore voxels surrounding a pore space to pore voxels, wherein the digital pore growing operation is based at least in part on a predetermined dead oil estimate. The method also includes estimating a property of the rock sample based at least in part on the modified set of voxels.

20 Claims, 4 Drawing Sheets

(56) References Cited

U.S. PATENT DOCUMENTS

2014/0052420 A1     2/2014   Cavanaugh
2016/0049204 A1     2/2016   Watanabe et al.

OTHER PUBLICATIONS

Voutilainen, M., et al. "Pore-space characterization of an altered tonalite by X-ray computed microtomography and the 14C-labeled-polymethylmethacrylate method." Journal of Geophysical Research: Solid Earth 117.B1 (2012).*

Beckingham, Lauren E., et al. "2D and 3D imaging resolution trade-offs in quantifying pore throats for prediction of permeability." Advances in water resources 62 (2013): 1-12.*

Crandell, L. E., et al. "Changes in the pore network structure of Hanford sediment after reaction with caustic tank wastes." Journal of contaminant hydrology 131.1 (2012): 89-99.*

"International Search Report and Written Opinion", dated Dec. 11, 2015 Digital Pore Alteration Methods and Systems Appln. No. PCT/US2015/051749 filed Sep. 23, 2015, 14 pgs.

Brian Driskill, Joel Walls, Steven W. Sinclair, Juliana Devito; 2013, Applications of SEM imaging to reservoir characterization in the Eagle Ford Shale, south Texas, U.S.A., in W. Camp, E. Diaz, and B. Wawak, eds., Electron microscopy of shale hydrocarbon reservoirs: AAPG Memoir 102, p. 115-136.

MacLean O. Amabeoku, Saudi Aramco, Tariq M. Al-Ghamdi, Yaoming Mu, Ingrain and Jonas Toelke; Evaluation and Application of Digital Rock Physics (DRP) for Special Core Analysis in Carbonate Formations; Presentation at International Petroleum Technology Conference in Beijing, China on Mar. 2013; 13 pages.

\* cited by examiner

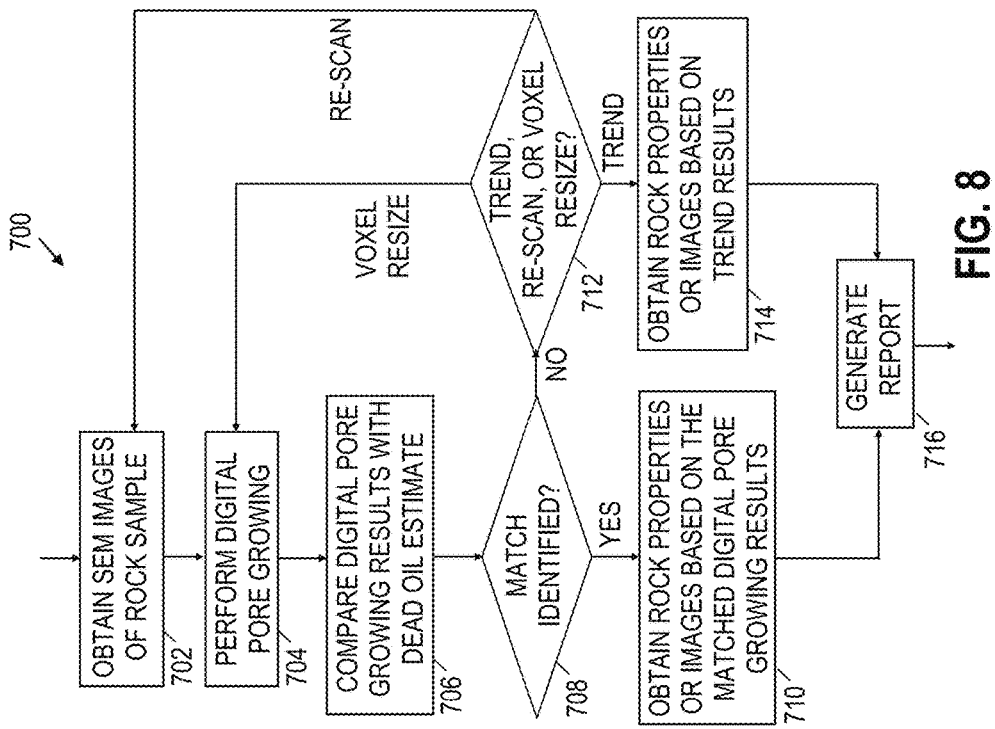
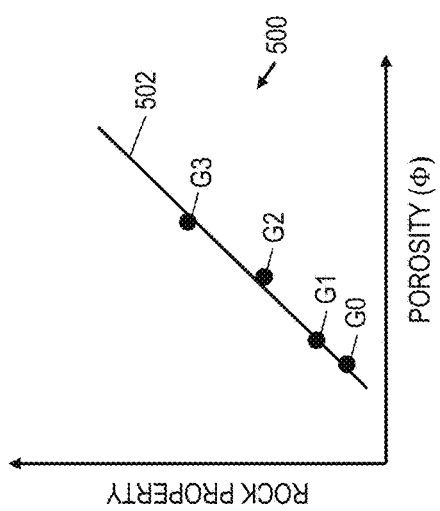
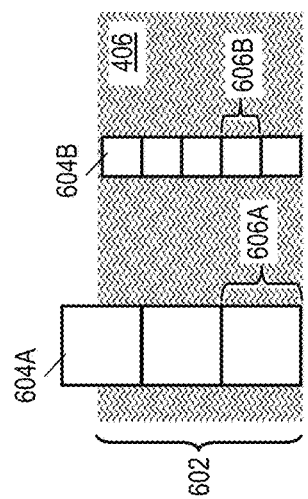

DIGITAL PORE ALTERATION METHODS AND SYSTEMS

CROSS-REFERENCE TO RELATED APPLICATIONS

The present application claims priority to U.S. Pat. App. 62/055,242 titled "Digital Pore Alteration Methods and Systems", filed Sep. 25, 2014 by inventors Joel Walls and Abraham Grader, which is incorporated by reference in its entirety.

BACKGROUND

Many conventional reservoir rocks have substantial amounts of crude oil in the pore system when recovered. Over time this oil losses its lighter components to evaporation and what remains is called dead oil. For traditional core analysis the dead oil must be removed before proper results can be obtained for porosity, permeability and most other rock properties that involve storage capacity or fluid transport. Removing the dead oil often requires days, weeks, or even months of soaking and flushing with organic solvents. Many of the solvents used are potentially hazardous either from toxicity, flammability, or both. In addition, solvent extraction may remove bitumen which could lead to overestimation of porosity and permeability in organic rich shales.

Digital rock physics (DRP) uses scanning electron microscope (SEM) images to determine many rock properties of interest without requiring the above-mentioned core cleaning process. This is possible, in part, due to the contrast in density and X-ray attenuation between dead oil and rock framework minerals. For example, even for a conventional core sample that has not been cleaned, DRP analysis is able to count dead oil as pore space.

Available geochemistry data shows that there is a substantial ratio of oil to organic matter solids (OMS) or oil to total organic carbon (TOC) in shale samples, perhaps in the range of 20-30%. Conventional core cleaning of these shale samples is problematic due to their low permeability. DRP analysis of the shale samples is also problematic due to the dead oil being essentially indistinguishable from the OMS in SEM images of the shale samples. This is true whether using secondary electron or backscatter electron imaging. To the extent DRP analysis counts dead oil as OMS (or does not count dead oil as pore space), the accuracy of the porosity estimate as well as other rock properties of a shale sample decreases.

BRIEF DESCRIPTION OF THE DRAWINGS

Accordingly, there are disclosed herein digital pore growing methods and systems. In the drawings:

FIG. 6 is a graph showing an illustrative digital pore growing trend.

FIG. 7 is a perspective view showing illustrative voxel sizes relative to a layer of dead oil.

FIG. 8 is a flowchart showing an illustrative digital pore growing method.

Figure 1:
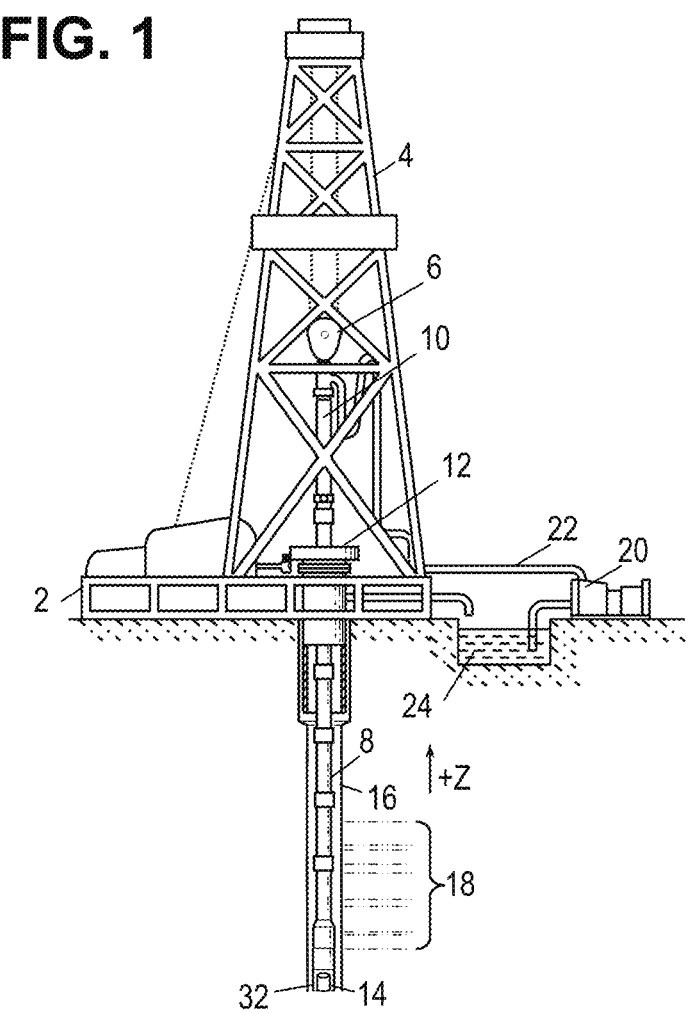
FIG. 1 is a schematic diagram showing an illustrative drilling environment.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Disclosed herein are improved methods and systems for digital pore growing, where the presence of dead oil is accounted for. In accordance with at least some embodiments, digital pore growing involves obtaining scanning electron microscope (SEM) images of a rock sample. The images are used to build a volume of data points (voxels) representing the pores and matrix of the scanned rock sample. Because SEM images do not distinguish between dead oil and organic matter solids (OMS), the initial volume of voxels representing the scanned rock sample will include voxels recognized as pores while all other voxels (including those corresponding to dead oil) are considered to be part of the matrix. As used herein, the term "organic matter solids" or "OMS" refers to kerogen, bitumen, pyrobitumen, or some combination thereof.

In at least some embodiments, performing digital pore growing involves changing a layer of matrix voxels surrounding a pore space to be pore voxels. The process of digital pore growing can be repeated such that multiple layers of matrix voxels around a pore space become pore voxels. For example, if three layers of matrix voxels are converted to pore voxels, the first layer (nearest to the original pore space) may be referred to as pore growth layer 1, the second layer may be referred to as pore growth layer 2, and the third layer may be referred to as pore growth layer 3. Performing digital pore growing thus involves determining a suitable number of pore growth layers, where the pore growth layers are intended to represent an amount of estimated dead oil residing in each pore space of a scanned rock sample. It should be appreciated that the number of pore growth layers not only depends on a dead oil estimate, but also the voxel size. Further, it should be appreciated that the voxel size can be adjusted as needed and/or a rock sample can be re-scanned or digitally resampled as needed to obtain higher resolution images and/or representative digital volumes. Another alternative is to calculate a digital pore growth trend (e.g., a line or curve), where two or more pore growth layers are used to determine corresponding rock property values. With the pore growth trend, other rock property values can be estimated for pore growth values that are between or beyond the pore growth layers used to establish the pore growth trend.

In at least some embodiments, the dead oil estimate used to guide digital pore growing operations is obtained from one or more chemical analysis tests. In an example chemical analysis test, some or all of a rock sample is heated up such that gasses related to the chemical composition of the rock sample are released. The detected existence and relative concentration of particular chemicals in the rock sample can be correlated with a dead oil estimate (e.g., an amount of dead oil for the rock sample and/or the thickness of a dead oil layer lining pores of the rock sample). Such dead oil estimates can be used to guide digital pore growing operations for the rock sample. Further, such dead oil estimates may be subject to scaling or other adjustments determined to improve the accuracy of digital pore growing results.

In some scenarios, a rock sample is subject to SEM scanning before being subject to one or more chemical analysis tests that determine a dead oil estimate. Once the dead oil estimate is obtained for the rock sample, the digital volume for the scanned rock sample can be updated by performing digital pore growth operations based on the obtained dead oil estimate. Alternatively, a rock sample may be subject to SEM scanning after being subject to one or more chemical analysis tests that determine a dead oil estimate. In either case, digital pore growing operations related to a dead oil estimate can be performed to obtain a new digital volume or to modify an existing digital volume representing a scanned rock sample. Further, it should be appreciated that a dead oil estimate obtained for one rock sample may be used to perform digital pore growing operations for another rock sample.

After digital pore growing operations are finalized, a new or modified digital volume can be analyzed to identify rock properties. Example rock properties include, but are not limited to, porosity, permeability, pore size(s), pore throat size(s), relative permeability, capillary pressure, and fluid flow characteristics. As desired, digital pore growing operations may include use of pore growth trends, voxel size adjustments, re-scanning of a rock sample, and/or re-testing of a dead oil estimate. Further, images or videos of a digital volume based on digital pore growing can be generated. Further, a scanned rock sample report may be generated, where rock property values, images, or videos included with the report are based on digital pore growing results. Further, a comparison of rock property values, images, or other information, with and without digital pore growing may be included in a report. Further, it should be appreciated that the digital pore growing operations and related images, videos, rock properties, and reports are relevant to two-dimensional as well as three-dimensional data sets.

While the disclosed methods and systems for pore alteration are directed to partial removal of OMS from 2D or 3D images, it should be appreciated that removal of solid mineral material is also possible. Further, it should be appreciated that pore alternation need not remove an equal number of voxels or layers around different pores of a 2D space or 3D volume. If desired a greater number of voxels or layers could be removed in some locations and a lesser number could be removed in others. Such variations could be applied to represent physical phenomena such as dissolution of solids by liquids for example. Further, the disclosed methods and systems for pore alteration could be extended to remove all OMS and/or to remove some or all of a particular mineral or other solid phase. Further, the disclosed methods and systems for pore alteration may be adjusted to reduce pore volume (instead of growing pore volume) by adding OMS or other solid phases.

Without limitation to other drilling arrangements, FIG. 1 shows an illustrative drilling environment. As shown, a drilling platform 2 supports a derrick 4 having a traveling block 6 for raising and lowering a drill string 8. A kelly 10 supports the drill string 8 as it is lowered through a rotary table 12. A drill bit 32 is driven by a downhole motor and/or rotation of the drill string 8. As bit 32 rotates, it creates a borehole 16 that passes through various formations 18. In some drilling scenarios, a pump 20 circulates drilling fluid through a feed pipe 22 to kelly 10, downhole through the interior of drill string 8, through orifices in drill bit 32, back to the surface via the annulus around drill string 8, and into a retention pit 24. The drilling fluid transports cuttings from the borehole into the pit 24 and aids in maintaining the borehole integrity.

In addition to producing cuttings, the drill bit 32 also may collect a rock core sample 14 for later analysis as described herein. In various embodiments, downhole cutting tools such as drill bit 32 may collect rock core samples from any of the formations 18 along borehole 16 for later analysis. Additionally, cutting tools such as the drill bit 32 (or supplemental cutting tools along drill string 8) may extend in different directions (e.g., angled or horizontal) along the borehole 16 to collect sidewall core rock samples. The process of drilling for rock core samples may occur while the borehole 16 is being drilled or afterwards. More generally speaking, the rock core sample 14 may correspond to sidewall cores, whole cores, drill cuttings, outcrop quarrying samples, or other sample sources which can provide suitable samples for analysis using methods of the present disclosure.

Figure 2:
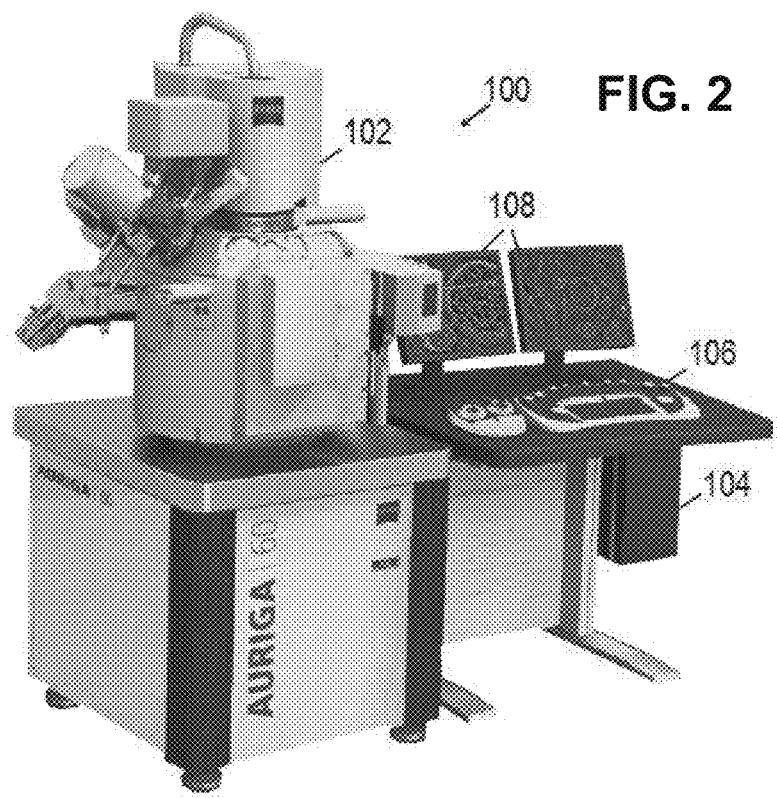
FIG. 2 is a schematic diagram showing an illustrative focused ion beam scanning electron microscope (FIB-SEM) system.

FIG. 2 provides an illustration of a high-resolution focused ion beam scanning electron microscope (FIB-SEM) 100 having an observation chamber 102 in which a sample of material is placed. A computer 104 is coupled to the observation chamber instrumentation to control the measurement process. Software on the computer 104 interacts with a user via a user interface having one or more input devices 106 (such as a keyboard, mouse, joystick, light pen, touchpad, or touchscreen) and one or more output devices 108 (such as a display or printer).

For high resolution imaging, the observation chamber 102 is typically evacuated of air and other gases. A beam of electrons or ions can be rastered across the sample's surface to obtain a high resolution image. Moreover, the ion beam energy can be increased to mill away thin layers of the sample, thereby enabling sample images to be taken at multiple depths. When stacked, these images offer a three-dimensional image of the sample to be acquired. As an illustrative example of the possibilities, some systems enable such imaging of a 40×40×40 micrometer cube at a 10 nanometer resolution.

The system described above is only one example of the technologies available for imaging a sample. Transmission electron microscopes (TEM) and three-dimensional tomographic x-ray transmission microscopes are two other technologies that can be employed to obtain a digital model of the sample. Regardless of how the images are acquired, the following disclosure applies so long as the resolution is sufficient to reveal the porosity structure of the sample.

The source of the sample, such as in the instance of a rock formation sample, is not particularly limited. For rock formation samples, for example, the sample can be sidewall cores, whole cores, drill cuttings, outcrop quarrying samples, or other sample sources which can provide suitable samples for analysis using methods according to the present disclosure.

Figure 3:
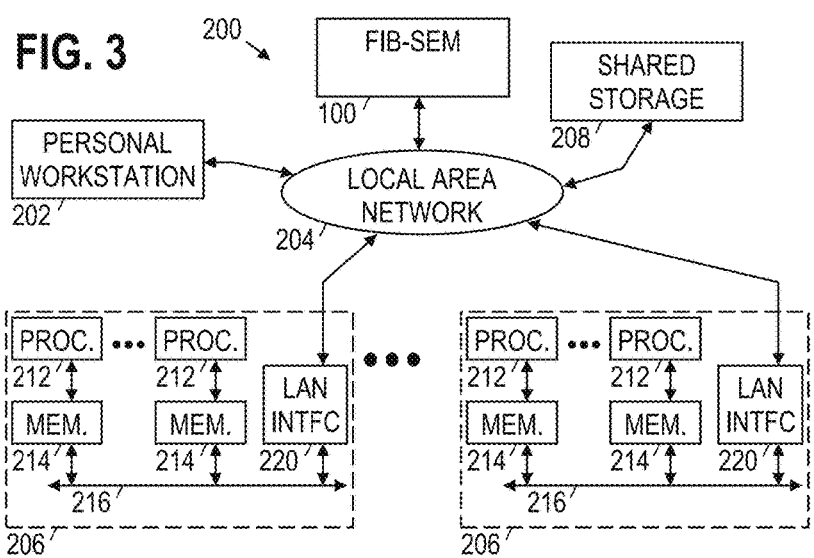
FIG. 3 is a block diagram showing an illustrative high performance computing network.

FIG. 3 is an example of a larger system 200 within which the FIB-SEM 100 can be employed. In the larger system 200, a personal workstation 202 is coupled to the FIB-SEM 100 by a local area network (LAN) 204. The LAN 204 further enables intercommunication between the FIB-SEM 100, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the FIB-SEM 100. For tasks having small computational demands, the software may be executed on the personal workstation 202, whereas computationally demanding tasks may be preferentially run on the high performance computing platform 206.

Figure 4:
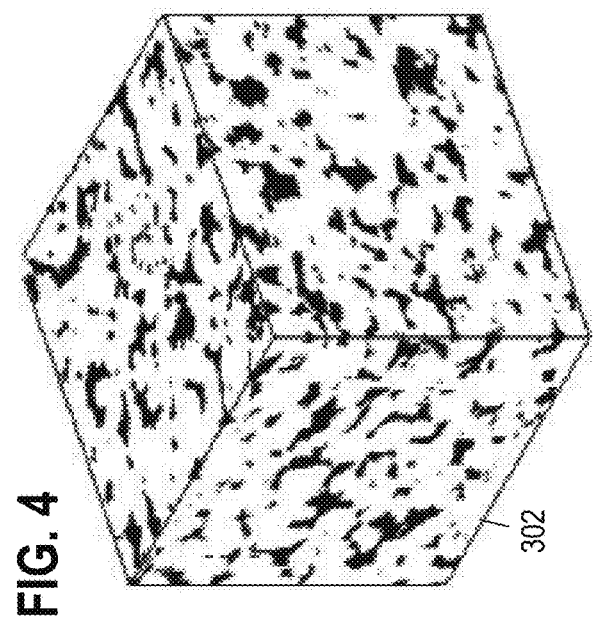
FIG. 4 is a perspective view showing an illustrative volumetric representation of a sample.

FIG. 4 is an illustrative digital volume 302 that might be acquired using images obtained from the scanning microscope 100. The digital volume 302 is made up of three-dimensional volume elements referred to as voxels, each having a value indicative of the composition of a rock sample at that point.

Figure 5:
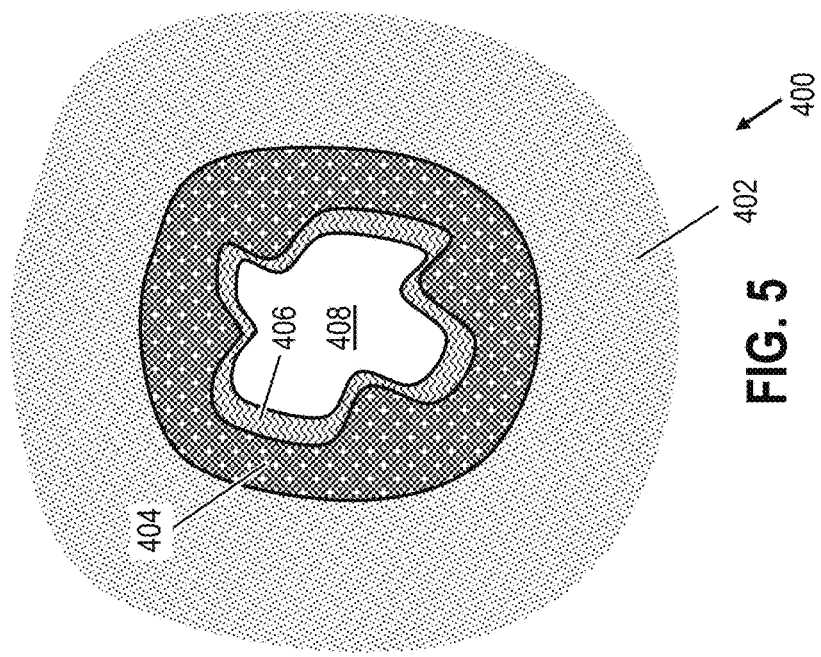
FIG. 5 is a cross-sectional view showing an illustrative digital pore space.

FIG. 5 is a cross-sectional view showing an illustrative pore space 408 of a digital volume such as digital volume 302. The pore space 408 resides within a volume of rock 402 and OMS 404. Further, a layer of dead oil 406 is assumed to exist between the OMS 404 and the pore space 408. Without the disclosed digital pore growing operations, the digital volume 302 identifies the layer of dead oil 408 as part of the rock matrix (e.g., OMS 404 or rock 402). However, the layer of dead oil 406 is a result of extracting a rock sample from its original downhole environment. Accordingly, in at least some embodiments, DRP analysis for a digital volume includes performing digital pore growing operations, where the amount of digital pore growing operations is determined at least in part by a dead oil estimate. In this manner, rock properties and related reports for a scanned rock sample consider the layer of dead oil 406 as if it were pore space 408.

In at least some embodiments, digital pore growing operations include calculating a digital pore growth trend. FIG. 6 shows a graph 500 representing a digital pore growth trend 502 determined from the original image or volume (G0) and/or three pore growth layer data points (G1, G2, G3). The G0 data point corresponds to a porosity estimate and related rock property estimate without pore growing. The G1 data point corresponds to a porosity estimate and related rock property estimate when one layer of voxels surrounding a pore space is converted to pore space. The G2 data point corresponds to a porosity estimate and related rock property estimate when two layers of voxels surrounding a pore space are converted to pore space. The G3 data point corresponds to a porosity estimate and related rock property estimate when three layers of voxels surrounding a pore space are converted to pore space. The digital pore growth trend 502 corresponds to a line or curve fitted to at least some of the available pore growth layer data points. The rock property represented in graph 500 as a function of porosity may correspond to, for example, permeability, pore size, pore throat size, relative permeability, capillary pressure, or fluid flow characteristics. The digital pore growth trend 502 can be used to estimate porosities and rock properties that are between or beyond the available pore growth layer data points.

FIG. 7 is a perspective view showing illustrative voxel sizes relative to a layer of dead oil such as layer 406 described for FIG. 5. In FIG. 7, the layer 406 is shown to have a thickness 602. If digital pore growing is performed when voxels 604A have voxel size 606A, the digital pore growing result (while better than performing no digital pore growing) will be offset from the thickness 602 of dead oil layer 406 by up to half of voxel size 606A. As desired, a different voxel size can be selected. For example, when voxels 604B have voxel size 606B, the digital pore growing result can closely represent the thickness 602 of dead oil layer 406. As desired, voxel sizes can be adjusted and/or rock samples can be re-scanned to obtain higher resolution images. Further, digital pore growth trends such as trend 502 can be calculated or adjusted using different voxel sizes. Once a particular voxel size and/or digital pore growth trend 502 is determined to provide a suitable digital pore growing result, a digital area or volume based on the digital pore growing results can be evaluated to determine rock properties, images, videos, and/or related reports. Example rock properties include, but are not limited to, porosity, permeability, pore size(s), pore throat size(s), relative permeability, capillary pressure, and fluid flow characteristics. An example porosity estimate for part or all of the scanned rock sample can be calculated (after digital pore growing results) as the ratio of voxels identified as pore space over all voxels. If different portions of the rock sample are identified as having a different structure (e.g., a heterogeneous rock sample), a separate porosity estimate can be identified for each representative portion of the rock sample. Once one or more porosity estimates are obtained for the rock sample, various correlations or models can be applied to obtain estimates for permeability, pore size(s), pore throat size(s), relative permeability, capillary pressure, and fluid flow characteristics. For more information regarding estimation of porosity and/or other parameters in a digital rock physics (DRP) environment, reference may be had to Maclean O. Amabeoku et al., *Evaluation and Application of Digital Rock Physics (DRP) for Special Core Analysis in Carbonate Formation*, International Petroleum Technology Conference, 26-28 March, Beijing, China (2013), and to Brian Driskill et al., 11 *Applications of SEM imaging to reservoir characterization in the Eagle Ford Shale*, south Texas, U.S.A., AAPG Memoir 102, p. 115-136 (2013).

The rock properties, images, videos, and/or related reports based at least in part on digital pore growing as described herein, can be associated with the scanned rock sample and/or a formation from which the rock sample was taken. As desired, the rock properties, images, videos, and/or related reports based at least in part on digital pore growing as described herein can be compared with laboratory rock sample analysis results to obtain comparison results regarding rock properties of the rock sample. A user or client may use the rock properties, images, videos, and/or related reports based at least in part on digital pore growing and/or comparison results to make hydrocarbon exploration or production decisions (e.g., the number and position of wells in a formation, well completion options, and/or related operations).

FIG. 8 is a flowchart showing an illustrative digital pore growing method 700. The method 700 may be performed by a computer system such as computer 60 or computer platform 206. As shown, the method 700 starts by receiving SEM images of a rock samples before (block 702). Digital pore growing is subsequently performed for a digital volume representing the scanned rock sample (block 704). Different digital pore growing results are compared with a dead oil estimate (block 706). For example, the dead oil estimate may be obtained by performed a chemical analysis test on the rock sample (or a related rock sample) before or after a rock sample is scanned. If a match is identified (decision block 708), rock properties or images are obtained based on the matched digital pore growing results (block 710). Further, a related report may be generated at block 716. The report generated at block 716 may include rock properties, images, videos, and/or charts based at least in part on the digital pore growing results. A user or client may use the report and/or may compare the report with laboratory rock sample analysis results to make hydrocarbon exploration or production decisions (e.g., the number and position of wells in a formation, well completion options, and/or related operations).

If a match is not identified (decision block 708), a digital pore growth trend, re-scan, or voxel resize decision is made (decision block 712). If use of a digital pore growth trend is selected at decision block 712, rock properties or images are obtained based on the digital pore growth trend results. If use of a different voxel size is selected at decision block 712, the digital volume is adjusted based on a new voxel size, and the method 700 returns to block 704. If re-scanning is selected at decision block 712, a higher resolution scan of a rock sample is performed, and the method 700 returns to block 702.

For explanatory purposes, the operations of the foregoing processes and method have been described as occurring in an ordered, sequential manner, but it should be understood that at least some of the operations can occur in a different order, in parallel, and/or in an asynchronous manner.

Embodiments disclosed herein include:

A: A method that comprises receiving images of a rock sample. The method also comprises modifying a set of voxels related to one or more of the received images by applying a digital pore growing operation that changes non-pore voxels surrounding a pore space to pore voxels, wherein the digital pore growing operation is based at least in part on a predetermined dead oil estimate. The method also comprises estimating a property of the rock sample based at least in part on the modified set of voxels.

B: A system that comprises a memory having software and one or more processors coupled to the memory to execute the software. The software causes the one or more processors to receive images of a rock sample and a predetermined dead oil estimate. The software further causes the one or more processors to modify a set of voxels related to one or more of the received images by applying a digital pore growing operation that changes non-pore voxels surrounding a pore space to pore voxels, wherein the digital pore growing operation is based at least in part on the predetermined dead oil estimate. The software further causes the one or more processors to estimate a property of the rock sample based at least in part on the modified set of voxels.

Each of the embodiments, A and B, may have one or more of the following additional elements in any combination. Element 1: wherein the predetermined dead oil estimate is based on a chemical analysis test. Element 2: wherein the chemical analysis test comprises detecting existence or concentration of one or more gasses released from the rock sample while the rock sample is heated. Element 3: wherein the digital pore growing operation comprises performing an adjustment operation in response to determining that a first pore growth does not match the predetermined dead oil estimate to within a threshold tolerance. Element 4: wherein the adjustment operation comprises using a pore growth trend to adjust the modified set of voxels or to estimate the property of the rock sample. Element 5: further comprising identifying and using the pore growth trend to estimate the property of the rock sample for pore growth values that are between two pore growth layers used to establish the pore growth trend. Element 6: further comprising using the pore growth trend to estimate the property of the rock sample for pore growth values that are beyond all pore growth layers used to establish the pore growth trend. Element 7: wherein the adjustment operation comprises reducing a voxel size and performing another digital pore growing operation based on the reduced voxel size. Element 8: wherein the adjustment operation comprises re-scanning images of the rock sample to obtain higher resolution images, and then applying another digital pore growing operation to a set of voxels related to one or more of the re-scanned images. Element 9: further comprising generating the set of voxels as a two-dimensional data set based on one or more of the received images. Element 10: further comprising generating the set of voxels as a three-dimensional data set based on a plurality of the received images.

Element 11: wherein the predetermined dead oil estimate is based on a chemical analysis test. Element 12: wherein the software further causes the one or more processors to perform an adjustment operation in response to determining that a first pore growth does not match the predetermined dead oil estimate to within a threshold tolerance. Element 13: wherein the adjustment operation comprises identifying and using a pore growth trend to adjust the modified set of voxels or to estimate the property of the rock sample. Element 14: wherein the software further causes the one or more processors to use the pore growth trend to estimate the property of the rock sample for pore growth values that are between two pore growth layers used to establish the pore growth trend. Element 15: wherein the software further causes the one or more processors to use the pore growth trend to estimate the property of the rock sample for pore growth values that are beyond all pore growth layers used to establish the pore growth trend. Element 16: wherein the adjustment operation comprises reducing a voxel size and performing another digital pore growing operation based on the reduced voxel size. Element 17: wherein the adjustment operation comprises re-scanning images of the rock sample to obtain higher resolution images, and then applying another digital pore growing operation to a set of voxels related to one or more of the re-scanned images. Element 18: wherein the software further causes the one or more processors to generate the set of voxels as a two-dimensional data set based on one or more of the received images.

Numerous variations and modifications will become apparent to those skilled in the art once the above disclosure is fully appreciated. In some embodiments, SEM scanning, digital pore growing operations, and dead oil estimation are performed by a single entity. Alternatively, one of more of the SEM scanning, digital pore growing, and dead oil estimation described herein may be performed by different entities. Further, it should be appreciated that the disclosed pore alternation methods and systems are applicable with other rock sample scanning technologies besides FIB-SEM. It is intended that the following claims be interpreted to embrace all such variations and modifications.

What is claimed is:

1. A method that comprises:
   receiving images of a rock sample;
   building a volume of voxels from the images;
   modifying a set of the voxels by applying a digital pore
      growing operation that changes non-pore voxels surrounding a pore space to pore voxels, wherein the digital pore growing operation is based at least in part on a predetermined dead oil estimate indicating that the non-pore voxels that are changed represent a dead oil and/or bitumen layer surrounding the pore space within the rock sample; and estimating a property of the rock sample based at least in part on the modified set of voxels.

2. The method of claim 1, wherein the predetermined dead oil estimate is based on a chemical analysis test.

3. The method of claim 2, wherein the chemical analysis test comprises detecting existence or concentration of one or more gasses released from the rock sample while the rock sample is heated.

4. The method of claim 1, wherein the digital pore growing operation comprises performing an adjustment operation in response to determining that a first pore growth does not match the predetermined dead oil estimate to within a threshold tolerance.

5. The method of claim 4, wherein the adjustment operation comprises using a pore growth trend to adjust the modified set of voxels or to estimate the property of the rock sample.

6. The method of claim 5, further comprising identifying and using the pore growth trend to estimate the property of the rock sample for pore growth values that are between two pore growth layers used to establish the pore growth trend.

7. The method of claim 5, further comprising using the pore growth trend to estimate the property of the rock sample for pore growth values that are beyond all pore growth layers used to establish the pore growth trend.

8. The method of claim 4, wherein the adjustment operation comprises reducing a voxel size and performing another digital pore growing operation based on the reduced voxel size.

9. The method of claim 4, wherein the adjustment operation comprises re-scanning images of the rock sample to obtain higher resolution images, and then applying another digital pore growing operation to a set of voxels related to one or more of the re-scanned images.

10. The method of claim 1, further comprising generating the set of voxels as a two-dimensional data set based on one or more of the received images.

11. The method of claim 1, further comprising generating the set of voxels as a three-dimensional data set based on a plurality of the received images.

12. A system that comprises:
a memory having software; and
one or more processors coupled to the memory to execute the software, the software causing the one or more processors to:

receive images of a rock sample and a predetermined dead oil estimate for the rock sample;

build a volume of voxels from the images; and modify a set of the voxels by applying a digital pore growing operation that changes non-pore voxels surrounding a pore space to pore voxels, wherein the digital pore growing operation is based at least in part on the predetermined dead oil estimate indicating that the non-pore voxels that are changed represent a dead oil and/or bitumen layer surrounding the pore space; and estimate a property of the rock sample based at least in part on the modified set of voxels.

13. The system of claim 12, wherein the software further causes the one or more processors to perform an adjustment operation in response to determining that a first pore growth does not match the predetermined dead oil estimate to within a threshold tolerance.

14. The system of claim 13, wherein the adjustment operation comprises identifying and using a pore growth trend to adjust the modified set of voxels or to estimate the property of the rock sample.

15. The system of claim 14, wherein the software further causes the one or more processors to use the pore growth trend to estimate the property of the rock sample for pore growth values that are between two pore growth layers used to establish the pore growth trend.

16. The system of claim 14, wherein the software further causes the one or more processors to use the pore growth trend to estimate the property of the rock sample for pore growth values that are beyond all pore growth layers used to establish the pore growth trend.

17. The system of claim 13, wherein the adjustment operation comprises reducing a voxel size and performing another digital pore growing operation based on the reduced voxel size.

18. The system of claim 13, wherein the adjustment operation comprises re-scanning images of the rock sample to obtain higher resolution images, and then applying another digital pore growing operation to a set of voxels related to one or more of the re-scanned images.

19. The system of claim 12, wherein the software further causes the one or more processors to generate the set of voxels as a two-dimensional data set based on one or more of the received images.

20. The system of claim 12, wherein the software further causes the one or more processors to generate the set of voxels as a three-dimensional data set based on a plurality of the received images.

* * * * *